(12) United States Patent
Kirby

(10) Patent No.: US 7,798,143 B1
(45) Date of Patent: Sep. 21, 2010

(54) RESPIRATORY TREATMENT DEVICE WITH PATIENT REPORTING

(75) Inventor: Todd Kirby, Spring Church, PA (US)

(73) Assignee: RIC Investments, LLC, Wilmington, DE (US)

( * ) Notice: Subject to any disclaimer, the term of this patent is extended or adjusted under 35 U.S.C. 154(b) by 1112 days.

(21) Appl. No.: 11/481,288

(22) Filed: Jul. 5, 2006

Related U.S. Application Data

(60) Provisional application No. 60/697,129, filed on Jul. 7, 2005.

(51) Int. Cl.
A61M 11/00 (2006.01)
(52) U.S. Cl. .............................. 128/204.18; 128/204.21
(58) Field of Classification Search ............ 128/204.21, 128/204.24
See application file for complete search history.

(56) References Cited

U.S. PATENT DOCUMENTS

| 5,517,983 A | 5/1996 | Deighan et al. |
| 5,685,296 A | 11/1997 | Zdrjokowski et al. |
| 5,694,923 A | 12/1997 | Hete et al. |
| 5,715,812 A | 2/1998 | Deighan et al. |
| 5,881,723 A * | 3/1999 | Wallace et al. ......... 128/204.21 |
| 5,937,855 A | 8/1999 | Zdrjokowski et al. |
| 6,017,315 A | 1/2000 | Starr et al. |
| 6,910,481 B2 * | 6/2005 | Kimmel et al. ......... 128/204.23 |
| 2002/0020410 A1 * | 2/2002 | Rydin et al. ........... 128/200.24 |

* cited by examiner

Primary Examiner—Steven O Douglas
(74) Attorney, Agent, or Firm—Timothy A. Nathan

(57) ABSTRACT

One aspect of the invention relates to a patient treatment system that delivers a pressurized flow of breathable gas to a patient. The system comprises a baseline module, a treatment measurement module, and a report module. The baseline module determines a baseline amount of treatment the patient should receive from the patient treatment system during a first time interval. The treatment measurement module measures an amount of treatment received by the patient during a second time interval. The report module generates a treatment report based upon the measured amount of treatment received by the patient during the second time interval and the baseline amount of treatment the patient should receive during the first time interval.

22 Claims, 3 Drawing Sheets

RESPIRATORY TREATMENT DEVICE WITH PATIENT REPORTING

CROSS-REFERENCE TO RELATED APPLICATIONS

This application claims priority under 35 U.S.C. §119(e) from provisional U.S. patent application No. 60/697,129, filed Jul. 7, 2005 the contents of which are incorporated herein by reference.

BACKGROUND OF THE INVENTION

1. Field of the Invention

The invention relates to respiratory treatment systems.

2. Description of the Related Art

Patients that suffer from sleep disordered breathing are typically treated with a Positive Airway Pressure (PAP) device that provides a pressurized flow of breathing gas according to a predetermined mode of ventilation, such as continuous positive airway pressure, proportional positive airway pressure, and proportional assist ventilation, among others. The pressurized gas supports a patient's airway as the patient sleeps such that episodes of cessation of breathing that are associated with sleep disordered breathing are reduced or avoided.

PAP devices may be uncomfortable to the patient resulting in patients using their PAP device less than the recommended amount. A patient's usage of a PAP device is typically monitored and reported by the device, usually to a caregiver or insurance company, to ensure that the patient is actually using the device enough to receive the requisite amount of treatment. However, conventional methods of monitoring and reporting patient usage provide reports that are not readily understandable to patients. This tends to hinder patients from being able to track their own treatment status. Consequently, there exists a need for a PAP device that generates intuitive usage reports regarding usage of their PAP devices.

SUMMARY OF THE INVENTION

One aspect of the invention relates to a patient treatment system that delivers a pressurized flow of breathable gas to a patient. The system comprises a baseline module, a treatment measurement module, and a report module. The baseline module determines a baseline amount of treatment the patient should receive from the patient treatment system during a first time interval. The treatment measurement module measures an amount of treatment received by the patient during a second time interval. The report module generates a treatment report based upon the measured amount of treatment received by the patient during the second time interval and the baseline amount of treatment the patient should receive during the first time interval.

Another aspect of the invention relates to a method of reporting treatment received by a patient from a patient treatment system that delivers a pressurized flow of breathable gas. The method comprises determining a baseline amount of treatment the patient should receive over a first time interval, measuring an amount of treatment received by the patient during a second time interval, and generating a treatment report based upon the measured amount of treatment received by the patient during the second time interval and the baseline amount of treatment the patient should receive during the first time interval.

Another aspect of the invention relates to a patient treatment system that delivers a pressurized flow of breathable gas to a patient. The system comprises a baseline module, a treatment measurement module, and a report module. The baseline module determines a baseline amount of treatment the patient should receive from the patient treatment system. The treatment measurement module measures an amount of treatment received by the patient. The report module generates a patient perceivable report based on a comparison between the measured amount of treatment received by the patient and the baseline amount of treatment the patient should receive.

Another aspect of the invention relates to a method of reporting treatment received by a patient from a patient treatment system that delivers a pressurized flow of breathable gas. The method comprises determining a baseline amount of treatment the patient should receive from the patient treatment system, measuring an amount of treatment received by the patient, and generating a treatment report based on a comparison between the measured amount of treatment received by the patient and the baseline amount of treatment the patient should receive.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
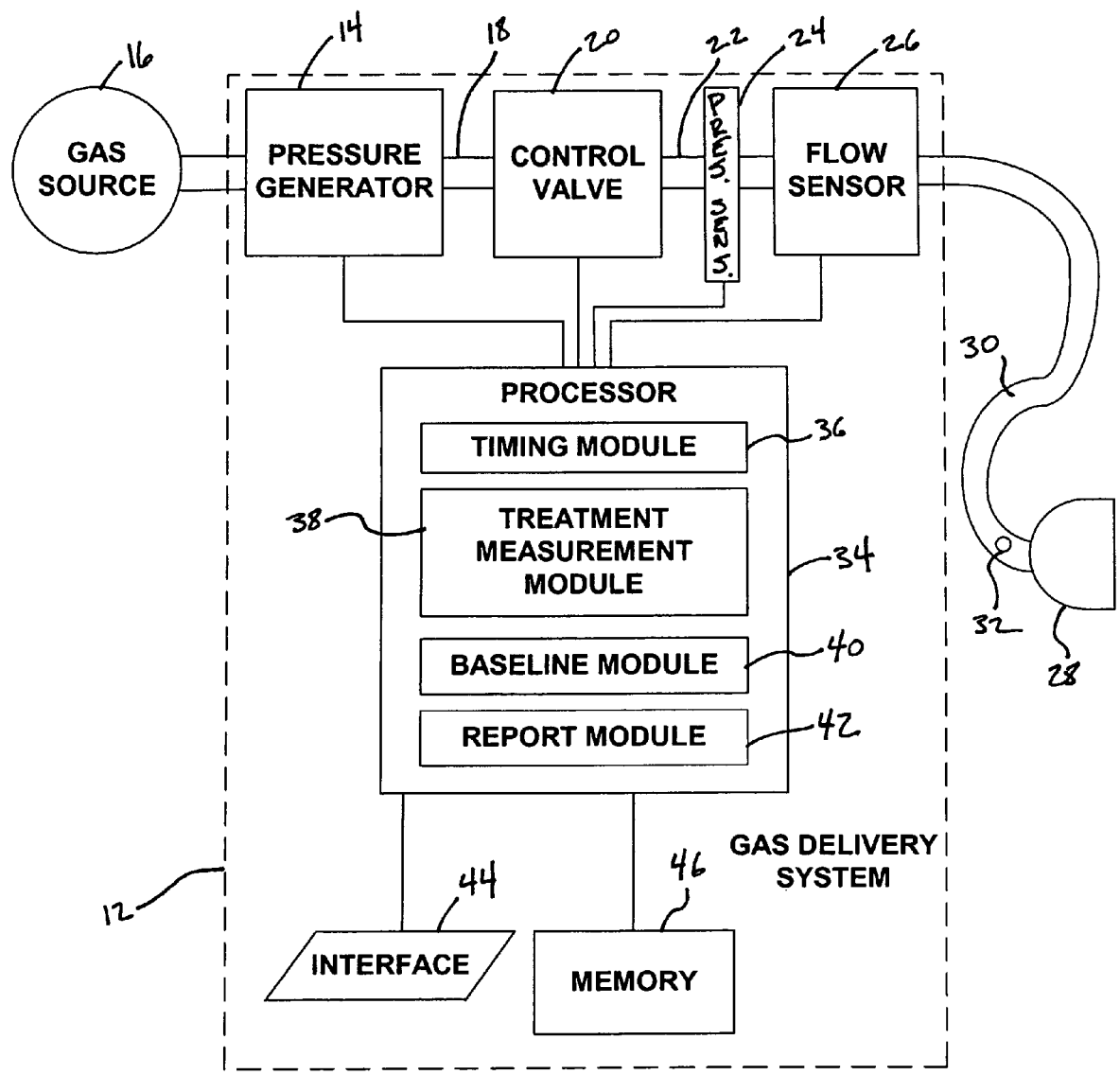
FIG. 1 illustrates a patient treatment system, in accordance with one embodiment of the invention.

FIG. 1 schematically illustrates an exemplary embodiment of a patient treatment system 10 according to the present invention. The patient treatment system 10 is capable of providing and automatically controlling the pressure of breathable gas delivered to a patient according to a predetermined mode of ventilation. Patient treatment system 10 includes a gas delivery system 12 that controls a flow of breathing gas to a patient. Gas delivery system 12 includes a pressure generator 14 that receives a supply of breathable gas from a breathable gas source 16, and elevates the pressure of that gas for delivery to the airway of a patient. Pressure generator 14 may include any device, such as a blower, a compressor (scroll, screw, or piston), or bellows that is capable of elevating the pressure of the received breathable gas from source 16 for delivery to a patient. In one embodiment of the present invention, pressure generator 14 is a blower that is driven at a constant speed during the course of the pressure support treatment to produce a constant pressure or flow rate at its output 18. According to one embodiment, gas source 16 is simply atmospheric air drawn into the system by pressure generator 14. In another embodiment, gas source 16 comprises a tank of pressurized gas connected with pressure generator 14. The tank of gas can contain any breathable gas, such as oxygen, air, or other mixture of breathable gas. The present invention also contemplates that a separate gas source 16 need not be used, but instead the pressure generator 14 can itself be defined by a canister or tank of pressurized gas, with the pressure delivered to the patient being controlled by a pressure regulator. In addition, while the embodiment of FIG. 1 illustrates a separate gas source 16, the present invention contemplates that gas source 16 can be considered to be part of the gas delivery system 12. Additionally, in another embodiment, the gas source 16 can be provided in the same housing as the rest of the gas delivery system 12. In yet another embodiment, an external gas source 16 provides the pressurized flow of breathable gas so as to constitute a pressure generator, thus eliminating the need for the separate pressure generator 14.

In the illustrated embodiment, gas delivery system 12 includes a control valve 20. The breathable gas is delivered to control valve 20, with an elevated pressure, downstream of the pressure generator 14. Control valve 20, either alone or in combination with pressure generator 14, controls the final pressure or flow of gas from exit 22 exiting the gas delivery system 12. Examples of a suitable control valve 20 include at least one valve, such as sleeve or poppet valve, that exhausts gas from the patient circuit as a method of controlling the pressure in the patient circuit. U.S. Pat. No. 5,694,923 to Hete et al., the contents of which are incorporated herein by reference, teaches a dual poppet valve system suitable for use as control valve 20 that exhausts gas to atmosphere and restricts the flow of gas from the pressure generator 14 to the patient. Other suitable pressure/flow controllers are well known to those skilled in the art.

In embodiments in which pressure generator 14 is a blower that operates at all times at one speed, the control valve 20 alone can be used to control the final pressure and flow rate for the breathable gas output from control valve 20. However, as noted above, the present invention also contemplates controlling the operating speed of pressure generator 14 in combination with control valve 20 to control the final pressure and flow rate of the breathable gas delivered to the patient. For example, a pressure or flow rate close to the desired pressure or flow rate can be set by establishing an appropriate operating speed for pressure generator 14 along and by setting the opening in control valve 20 so that the two, operating together, determine the final pressure for the breathable gas at exit 22.

The pressure of the pressurized flow of breathable gas is measured by a pressure sensor 24. In the embodiment of FIG. 1, pressure sensor 24 is a single sensor unit disposed downstream of pressure generator 14 and control valve 20. However, in other embodiments, pressure sensor 24 may include a single sensor unit disposed elsewhere, such as at an inlet of control valve 20, or at a location downstream from gas delivery system 12. Alternatively, pressure sensor 24 may include a plurality of sensor units disposed at various locations within gas delivery system 12. Pressure sensor 24 may include any device, transducer, or devices, capable of measuring the pressure of the pressurized flow of breathable gas generated by gas delivery system 12.

In the embodiment of FIG. 1, gas delivery system 12 includes a flow sensor 26. The pressurized flow of breathable gas 22 output from control valve 20 is delivered to flow sensor 26, which measures the instantaneous volume (V) of gas delivered to the patient, and/or the instantaneous flow rate (V') of such gas to the patient, or both. Flow sensor 26 may include any device suitable for measuring these parameters, such as a spirometer, pneumotach, variable orifice transducer, or other conventional flow transducer. In the illustrated embodiment, flow sensor 26 is provided at a location relatively distant from a patient interface assembly 28, as will be described. For example, U.S. Pat. No. 6,017,315 to Starr et al., the contents of which are incorporated herein by reference, teaches a quantitative flow member that is located at the patient interface assembly 28. The present invention also contemplates, however, locating sensor 26 at any location along a patient circuit 30, as will also be described.

The flow of breathing gas is carried from gas delivery system 12 to the patient via patient circuit 30, which can be a single flexible conduit that carries the flow of breathing gas to a patient interface assembly 28. Alternatively, as described later, it may be a two-limb circuit. Patient interface assembly 28 may include either an invasive or non-invasive patient interface appliance for communicating the pressurized flow of breathable gas to the airway of the patient. For example, patient interface assembly 28 may include a nasal mask, nasal/oral mask, total face mask, nasal cannula, endotracheal tube, or tracheal tube. The patient interface assembly 28 may also include a headgear assembly, such as mounting straps or a harness, for removably fastening the patient interface appliance to the patient. In the illustrated embodiment, the patient interface assembly 28 and/or patient circuit 30 includes a suitable exhaust port 32 for exhausting gas from these components to ambient atmosphere. Exhaust port 32 is preferably a passive exhaust port in the form of a continuously open port that imposes a flow restriction on the exhaust gas to permit control of the pressure of gas within patient interface assembly 28. It is to be understood, however, that exhaust port 32 can be an active exhaust port that assumes different configurations to control the exhaust rate. Examples of suitable exhaust ports are taught, for example, in U.S. Pat. Nos. 5,685,296 and 5,937,855 both to Zdrojkowski et al. As shown, gas delivery system 12 includes a processor 34 that controls various operating aspects of gas delivery system 12. For example, the output of flow sensor 26 and pressure sensor 24 are provided to processor 34 for processing, if needed, to determine the pressure of the breathable gas, the instantaneous volume (V) of the pressurized flow of breathable gas, and/or the instantaneous flow rate (V') of the pressurized flow of breathable gas. In some instances, the processor 34 determines the instantaneous volume by integrating the flow rate measured by flow sensor 26. Because, in one embodiment, the flow sensor 26 may be located relatively far from the patient interface assembly 30, in order to determine the actual flow rate of gas to the patient taking into account, for example, leaks in patient circuit 30 and elsewhere in patient delivery system 10, processor 34 may receive the output from flow sensor 26 as an estimated flow. The processor 34 processes this estimated flow information, for example, by performing leak estimation, to determine the actual flow at the patient's airway, as is known to those skilled in the art.

In one embodiment of the invention, processor 34 generates a treatment report that represents a measured amount of treatment that a patient has received in the past and/or a goal amount of treatment that the patient should receive in the future to reach a baseline amount of treatment. In the embodiment shown in FIG. 1, processor 34 comprises a timing module 36 that delineates the passage of time. For example, timing module 36 may include a clock, or other mechanism that keeps track of time. In one embodiment, timing module 36 generates a signal that enables other modules and components included in patient treatment system 10 (e.g. other modules included in processor 34) to measure time. For example, in such an embodiment, timing module 36 may be a CMOS timer (e.g., a 555 timer), computer software, or any other mechanism suitable for generating a signal at predetermined, configurable intervals in a continuous manner.

In the embodiment shown in FIG. 1, processor 34 includes a treatment measurement module 38 that measures an amount of treatment received by the patient from patient treatment system 10. The treatment measurement module 38 may measure the amount of treatment in terms of a usage parameter such as, for example, an amount of time patient treatment system 10 is in operation, an amount of time the pressurized flow of breathable gas is generated by gas delivery system 12, an amount of time the pressurized flow of breathable gas is received by the patient which may determined by monitoring whether gas delivery system 12 is operating and whether the patient interface assembly 28 is in position on the patient as determined, for example, by a pressure sensor disposed on a surface of the patient interface assembly 28 that detects contact between the patient and the surface of the patient interface assembly 28, an amount of breathable gas delivered by gas delivery system 12 as determined by flow sensor 26, an amount of breathable gas received by the patient as determined by a flow sensor disposed within patient interface assembly 28 or within patient circuit 30 proximate to patient interface assembly 28, or in terms of another usage parameter. In one embodiment, the treatment measurement module 38 measures the amount of treatment received by the patient while simultaneously monitoring the passage of time. For example, the measurement module 38 may monitor the passage of time based on an output of timing module 36. Thus, the treatment measurement module 38 may measure the amount of treatment received by the patient over a specified time interval such as, in a non-limiting example, the amount of treatment received over a day, a week, a month, or another specified time period.

As is shown in FIG. 1, processor 34 comprises a baseline module 40 that contains information on the baseline amount of treatment the patient should receive from the patient treatment system during a specified time interval. For instance, the baseline module 40 may determine a baseline amount of treatment the patient should receive during a day, a week, a month, or during another time interval. The baseline module 40 may determine the baseline amount of treatment that the patient should receive in terms of a usage parameter such as, for example, an amount of time patient treatment system 10 is in operation, an amount of time the pressurized flow of breathable gas is generated by gas delivery system 12, an amount of time the pressurized flow of breathable gas is received by the patient, an amount of breathable gas delivered by gas delivery system 12, an amount of breathable gas received by the patient, or in terms of another usage parameter. In one embodiment, the baseline amount of treatment and/or the specified time interval may be determined based on information input to processor 34 (e.g., via control interface 44 described below) by an individual, such as the patient, a caregiver, an insurance provider, or other individuals. For example, a baseline amount of treatment that the patient should receive over a week may be input to processor 34.

As is illustrated in FIG. 1, processor 34 comprises a report module 42 that generates a treatment report. A treatment report may convey to an individual (e.g., the patient, a caregiver, insurance provider, etc.) the sufficiency of a measured amount of treatment the patient has received during a specific past time interval. In addition, or instead, the report may convey a goal amount of treatment that the patient should receive over a specific future time interval, according to a reporting scheme.

In one embodiment, report module 42 compares a baseline amount of treatment the patient should have received during a past time interval as determined by baseline module 40 to a measured amount of treatment received by the patient during the same past time interval as determined by measurement module 38, and generates a treatment report that represents the relationship between the baseline amount and the measured amount. For example, the treatment report may include a percentage of the baseline amount of treatment that was received by the patient by dividing the measured amount of treatment by the baseline amount. Alternatively, the treatment report may include a ratio of the measured amount of treatment received by the patient to the baseline amount of treatment.

In another embodiment, a treatment report may convey to an individual a goal amount of treatment that the patient should receive during a future time interval. A goal amount may be determined from a baseline amount of treatment that the patient should receive during a first time interval and a measured amount of treatment that the patient has received during a second time interval, where the first time interval and the second time interval begin substantially simultaneously, but the second time interval is shorter than the first time interval. More particularly, the goal amount of treatment may be determined by subtracting the measured amount of treatment from the baseline amount of treatment. In such an instance, the future time interval during which the patient should receive the goal amount of treatment would be the time interval from the end of the second time interval to the end of the first time interval. For example, if a patient should receive X amount (baseline amount) of treatment in a week (first time interval), and has received Y amount (measured amount) of treatment in the first two days (second time interval) of the week, the goal amount of treatment that the patient should receive for the remainder of the week (future time interval) would be X−Y.

In one embodiment, generating the report may include determining an average goal amount of treatment that the patient should receive for each of a series of predetermined time intervals within the time interval between the end of the second time interval and the end of the first time interval in order to receive that baseline amount of treatment by the end of the first time interval. For instance, in the example described above where the goal amount for the final five days of the week was determined to be X−Y, an average daily goal amount is determined by dividing the goal amount of treatment by the remaining number of days (5). Thus, in this example, the average daily goal amount would be $$\frac{X-Y}{5}.$$

It should be appreciated that a variety of alternative reporting schemes for generating treatment reports can be provided outside of the ones indicated above. The scope of the invention contemplates the generation of any treatment report that is based upon a measured treatment amount and a baseline treatment amount, and conveys to an individual one or both of the sufficiency of a measured amount of treatment the patient has received during a specific past time interval and/or a goal amount of treatment that the patient should receive over a specific future time interval. Further, the invention contemplates reporting schemes in which treatment reports include messages that provide encouragement (e.g. "Keep it up, you are on track to reach your treatment goal."), congratulations (e.g. "Great job, you reached your treatment goal."), and/or warnings (e.g., "If you do not increase your usage, you will not reach your treatment goal."), or other linguistic messages that relate to the amount of treatment that a patient has and/or should receive. Such messages can, for example, be visual and be displayed on a display screen, or can be auditory and projected from a speaker, or any other humanly perceptible manner.

It may further be appreciated that the various modules 36, 38, 40, and 42 of processor 34 may be implemented in hardware, software, firmware, or in some combination of hardware, software, and/or firmware. Additionally, although modules 36, 38, 40, and 42, are shown in FIG. 1 as being located in a single location, this need not be the case. In one embodiment, processor 34 is a plurality of separate processors located remotely from each other operating in conjunction, for example, over a network. In such an embodiment, some or all of modules 36, 38, 40, and 42 may be located remotely from each other.

A control interface 44 provides data and commands to processor 34 of gas delivery system 12. Control interface 44 may include any device suitable to provide information and/or commands to processor 34 via a hardwire or wireless connection. Typical examples of control interface 44 may include a keypad, keyboard, touch pad, mouse, microphone, switches, button, dials, or any other devices that allow a user to input information to the gas delivery system 12. Control interface 44 may also include one or more devices suitable to provide information related to patient treatment system 10 to an individual (e.g., a patient, a caregiver, etc.) such as, for example, a screen, a printer, one or more indicator lights, a speaker, or other devices that enable the provision of information to the individual. For example, treatment reports generated by processor 34 may be communicated via control interface 44. It should be appreciated that control interface 44 may be located at gas delivery system 12 or may be located remotely and communicate with processor 34 via an operative communications link (e.g., hardwired, wireless, etc.). In one embodiment, control interface 44 may be implemented as a Graphical User Interface (GUI) running on a computing terminal that communicates with processor 34 via a network, or other communications link.

The present invention contemplates that in an embodiment (not illustrated), the patient circuit 26 can be a two-limb circuit, which is common in conventional ventilators. In a two-limb circuit, the first limb, like patient circuit 26, delivers breathing gas to the patient, except that it lacks an exhaust port. Instead, the second limb carries the exhaust gases from the patient to ambient atmosphere. Typically, an active exhaust port in the second limb under the control of a processor (e.g. processor 34) provides the desired level of positive end expiratory pressure (PEEP) to the patient.

Processor 34 controls pressure generator 14 and the actuation of control valve 20, thereby controlling the pressure of the pressurized flow of breathable gas generated by the gas delivery system 12. In one embodiment, processor 34 comprises a processor that is suitably programmed with an algorithm or algorithms to calculate the pressure to be applied to the patient according to one of any one of various modes of ventilation. In addition, the processor 34 may be capable of controlling pressure generator 14 and/or control valve 20 based on data received from pressure sensor 24 and/or flow sensor 26 to apply the calculated pressure to the breathable gas within gas delivery system 12. In one embodiment of the present invention, the gas delivery system 12 includes a memory 46 associated with processor 34 for storing the programming used to perform any of a plurality of modes of ventilation, depending on which mode of ventilation is selected by the caregiver or patient using control interface 44. Memory 46 may also be capable of storing data regarding the operation of the gas delivery system 12, input commands, alarm thresholds, as well as any other information pertinent to the operation of the gas delivery system 12, such as measured values of gas flow, volume, pressure, device usage, operating temperatures, and motor speed.

Figure 2:
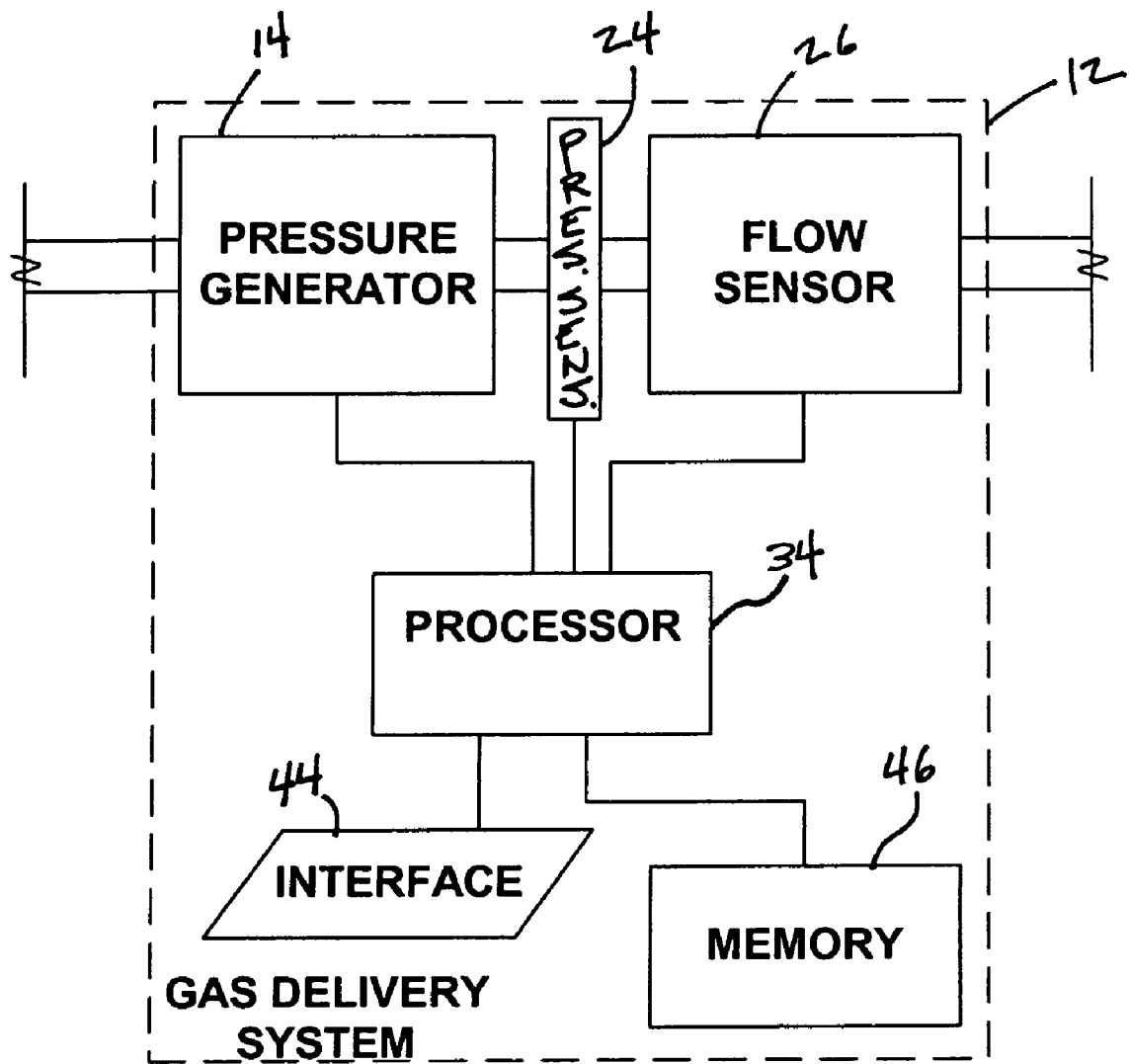
FIG. 2 illustrates a gas delivery system, according to one embodiment of the invention.

An alternative embodiment of gas delivery system 12 is discussed below with reference to FIG. 2. In FIG. 2, parts similar to corresponding parts in the embodiment of FIG. 1 are labeled with the same reference numerals. Unlike the embodiment of FIG. 1, the final pressure of the breathable gas is not controlled by a control valve, either alone or in combination with pressure generator 14. Instead, gas delivery system 12 controls the pressure of the breathable gas based only on the output of a pressure generator 14. For example, in one embodiment, pressure generator 14 is a blower and processor 34 (as described in the first embodiment) controls the pressure of the breathable gas delivered to the patient by controlling the motor speed of pressure generator 14. The present invention contemplates implementing the pressure of the breathable gas as measured by pressure sensor 24 and a speed monitor for the blower motor to provide feedback data to processor 34 for controlling the operation of pressure generator 14. In addition, gas delivery system 12 (as shown in either of FIG. 1 or 2) and related components may include other conventional devices and components, such as a humidifier, heater, bacteria filter, temperature sensor, humidity sensor, and a gas sensor (e.g., a capnometer), that filter, measure, monitor, and analyze the flow of gas to or from the patient.

Figure 3:
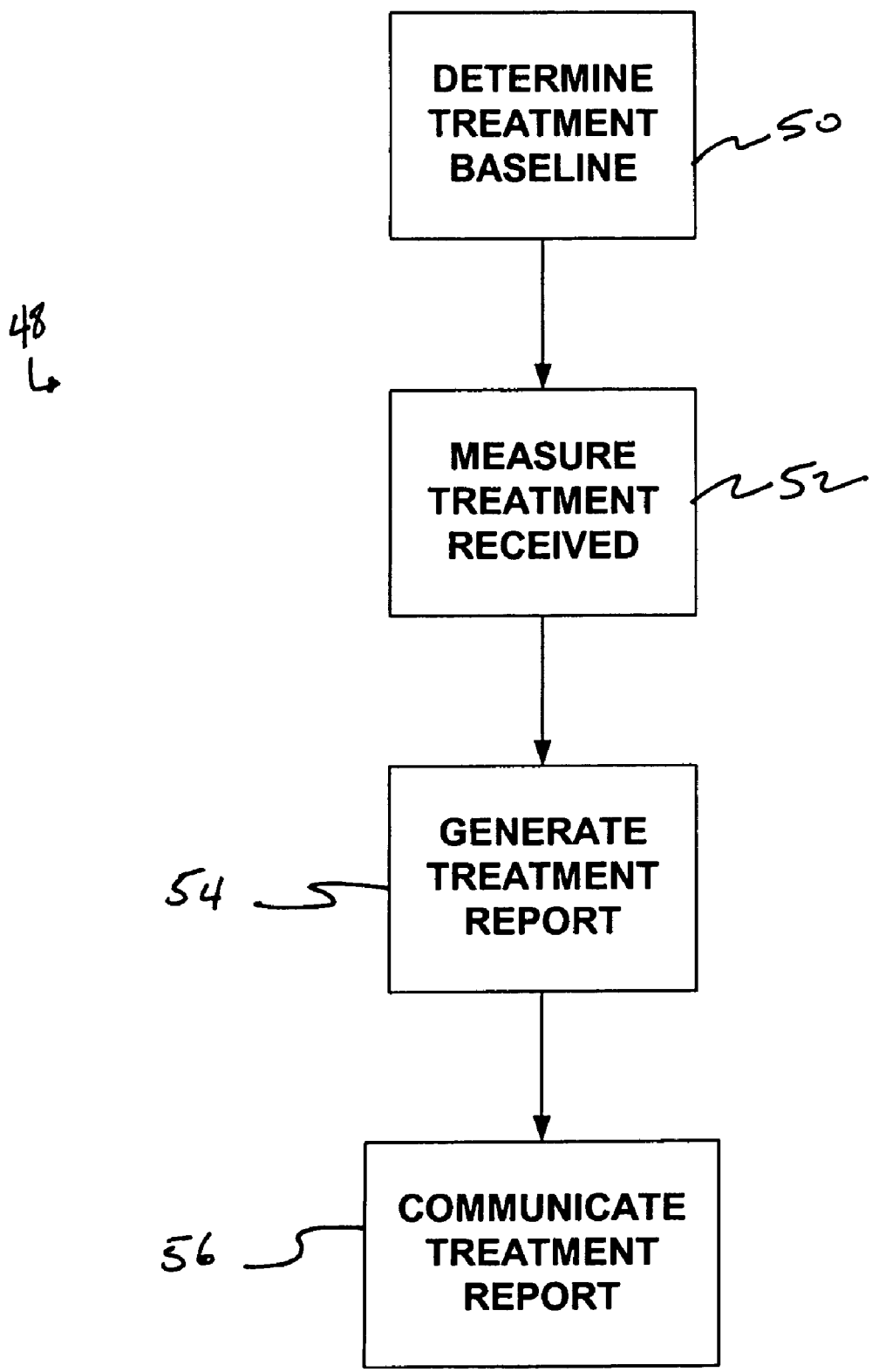
FIG. 3 illustrates a method of reporting treatment received by a patient from a patient treatment system that delivers a pressurized flow of breathable gas, in accordance with one embodiment of the invention.

FIG. 3 is an exemplary illustration of a method 48 of reporting treatment received by a patient from patient treatment system 10. In one embodiment, the steps of method 48 are executed by processor 34. At a step 50 a baseline amount of treatment the patient should receive from patient treatment system 10 during a first time interval is determined. In one embodiment, the baseline amount may be determined by baseline module 40 as described above. At a step 52 a measured amount of treatment received by the patient during a second time interval is measured. According to one embodiment, the measured amount is measured by treatment measurement module 38 as set forth above. At a step 54 a treatment report based upon the measured amount of treatment received by the patient during the second time interval and the baseline amount of treatment the patient should receive during the first time interval is generated. In one embodiment, the treatment report is generated by report module 42 as previously described. At a step 56, the treatment report is communicated to an individual. According to one embodiment, the treatment report is communicated to the individual, which may include the patient, a caregiver, or another individual, via control interface 44.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A patient treatment system that delivers a pressurized flow of breathable gas to a patient, the system comprising:
one or more processors configured to execute computer program modules, the computer program modules comprising:
a baseline module configured to determine, at the one or more processors, a baseline amount of time the patient should spend receiving treatment from the patient treatment system;
a treatment measurement module configured to measure, at the one or more processors, an amount of time spent by the patient receiving treatment from the patient treatment system;
a report module configured to generate, at the one or more processors, a patient perceivable report based on a comparison between the measured amount of time spent by the patient receiving treatment from the patient treatment system and the baseline amount of time the patient should spend receiving treatment from the patient treatment system.

2. The patient treatment system of claim 1, further comprising:
a control interface that communicates the treatment report to an individual.

3. A method of reporting treatment received by a patient from a patient treatment system that delivers a pressurized flow of breathable gas, the method being executed by one or more processors, the method comprising:
determining, by the one or more processors, a baseline amount of time the patient should spend receiving treatment from the patient treatment system;
measuring, by the one or more processors, an amount of time the patient spent receiving treatment from the patient treatment system; and
generating, by the one or more processors, a treatment report based on a comparison between the measured amount of time the patient spent receiving treatment from the patient treatment system and the baseline amount of time the patient should spend receiving treatment from the patient treatment system.

4. The method of claim 3, further comprising:
communicating, by the one or more processors, the treatment report to an individual.

5. A patient treatment system that delivers a pressurized flow of breathable gas to a patient, the system comprising:
one or more processors configured to execute computer program modules, the computer program modules comprising:
a baseline module that determines, at the one or more processors, a baseline amount of treatment the patient should receive from the patient treatment system during a first time interval,
a treatment measurement module that measures, at the one or more processors, an amount of treatment received by the patient during a second time interval, wherein the second time interval includes a different amount of time than the first time interval, and
a report module that generates, at the one or more processors, a treatment report based upon the measured amount of treatment received by the patient during the second time interval and the baseline amount of treatment the patient should receive during the first time interval.

6. The patient treatment system of claim 5, wherein the second time interval and the first time interval overlap such that the second time interval falls entirely within the first time interval.

7. The patient treatment system of claim 5, wherein the treatment report comprises a ratio of the measured treatment amount to the baseline treatment amount.

8. The patient treatment system of claim 5, wherein the treatment report comprises a percentage of the baseline treatment amount.

9. The patient treatment system of claim 6, wherein the second time interval and the first time interval begin substantially simultaneously, and the treatment report comprises a goal amount of treatment that the patient must receive between the end of the second time interval and the end of the first time interval in order to reach the baseline amount of treatment by the end of the first time interval.

10. The patient treatment system of claim 9, wherein the goal amount of treatment is determined by subtracting the measured amount of treatment from the baseline amount of treatment.

11. The patient treatment system of claim 5, wherein the treatment measurement module measures the amount of treatment received by the patient in terms of the amount of time that the patient is receiving treatment from the patient treatment system.

12. The patient treatment system of claim 5, wherein the treatment measurement module measures the amount of treatment received by the patient in terms of the amount of pressurized breathable gas received by the patient from the patient treatment system.

13. The patient treatment system of claim 5, further comprising:
a control interface that communicates the treatment report to an individual.

14. A method of reporting treatment received by a patient from a patient treatment system that delivers a pressurized flow of breathable gas, the method being executed by one or more processors, the method comprising:
determining, by the one or more processors, a baseline amount of treatment the patient should receive over a first time interval;
measuring, by the one or more processors, an amount of treatment received by the patient during a second time interval, wherein the second time interval includes a different amount of time than the first time interval; and
generating, by the one or more processors, a treatment report based upon the measured amount of treatment received by the patient during the second time interval and the baseline amount of treatment the patient should receive during the first time interval.

15. The method of claim 14, further comprising:
communicating, by the one or more processors, the treatment report to an individual.

16. The method of claim 14, wherein the second time interval and the first time interval overlap such that the second time interval falls entirely within the first time interval.

17. The method of claim 14, wherein the treatment report comprises a ratio of the measured treatment amount to the baseline treatment amount.

18. The method of claim 14, wherein the treatment report comprises a percentage of the baseline treatment amount.

19. The method of claim 16, wherein the second time interval and the first time interval begin substantially simultaneously, and the treatment report comprises a goal amount of treatment that the patient must receive between the end of the second time interval and the end of the first time interval in order to reach the baseline amount of treatment by the end of the first time interval.

20. The method of claim 19, wherein the goal amount of treatment is determined by subtracting the measured amount of treatment from the baseline amount of treatment.

21. The method of claim 14, wherein the amount of treatment received by the patient is measured in terms of the amount of time that the patient is receiving treatment from the patient treatment system.

22. The method of claim 14, wherein the amount of treatment received by the patient is measured in terms of the amount of pressurized breathable gas received by the patient from the patient treatment system.

* * * * *